(12) United States Patent  
Cool et al.

(10) Patent No.: US 8,520,932 B2  
(45) Date of Patent: Aug. 27, 2013

(54) 3D TISSUE MODEL FORMATION FROM NON-PARALLEL 2D IMAGES

(75) Inventors: Derek Cool, London (CA); Aaron Fenster, London (CA); Donal Downey, Kamloops (CA); Shi Sherebrin, London (CA)

(73) Assignee: The University of Western Ontario, Ontario (CA)

( * ) Notice: Subject to any disclaimer, the term of this patent is extended or adjusted under 35 U.S.C. 154(b) by 599 days.

(21) Appl. No.: 12/602,308

(22) PCT Filed: May 28, 2008

(86) PCT No.: PCT/IB2008/003129  
§ 371 (c)(1),  
(2), (4) Date: Apr. 28, 2010

(87) PCT Pub. No.: WO2009/019617  
PCT Pub. Date: Feb. 12, 2009

(65) Prior Publication Data  
US 2011/0299750 A1    Dec. 8, 2011

Related U.S. Application Data

(60) Provisional application No. 60/940,427, filed on May 28, 2007.

(51) Int. Cl.  
*G06K 9/00* (2006.01)  
*A61B 8/14* (2006.01)

(52) U.S. Cl.  
USPC ............................ 382/154; 382/128; 600/459

(58) Field of Classification Search  
USPC ......... 382/154, 128, 131, 132, 130; 600/300, 600/407, 437, 410, 411, 458, 459, 461, 425, 600/429, 562, 417; 434/264  
See application file for complete search history.

(56) References Cited

U.S. PATENT DOCUMENTS

| 7,916,976 B1 * | 3/2011 | Kedikian | 382/305 |
| 7,961,982 B2 * | 6/2011 | Sibiryakov et al. | 382/294 |
| 2003/0013951 A1 * | 1/2003 | Stefanescu et al. | 600/407 |
| 2006/0155761 A1 * | 7/2006 | Van De Sluis et al. | 707/104.1 |

FOREIGN PATENT DOCUMENTS

CA    2600981    8/2006

OTHER PUBLICATIONS

Cool, et al., "3D Prostate Model Formation from Non-Parallel 2D Ultrasound Biopsy Images", Medical Image Analysis, Dec. 2006, pp. 875-887, vol. 10, Issue 6.

Tutar, et al., "Semiautomatic 3-D Prostate Segmentation From TRUS Images Using Spherical Harmonics", IEEE Transactions on Medical Imaging, Dec. 2006, pp. 1645-1654, vol. 25, No. 12.

Carr, et al., "Reconstruction and Representation of 3 D Objects with Radial Basis Functions", Computer Graphics Annual Conference (SIGGRAPH 2001), 2001, pp. 67-76.

* cited by examiner

*Primary Examiner* — Sheela Chawan  
(74) *Attorney, Agent, or Firm* — Reed Smith LLP

(57) ABSTRACT

Biopsy of the prostate using 2D transrectal ultrasound (TRUS) guidance is the current gold standard for diagnosis of prostate cancer; however, the current procedure is limited by using 2D biopsy tools to target 3D biopsy locations. We have discovered a technique for patient-specific 3D prostate model reconstruction from a sparse collection of non-parallel 2D TRUS biopsy images. Our method can be easily integrated with current TRUS biopsy equipment and could be incorporated into current clinical biopsy procedures for needle guidance without the need for expensive hardware additions. We have demonstrated the model reconstruction technique using simulated biopsy images from 3D TRUS prostate images of 10 biopsy patients. This technique of model reconstruction is not limited to the prostate, but can be applied to the reconstruction of any tissue acquired with non-parallel 2-dimensional ultrasound images.

32 Claims, 13 Drawing Sheets

(a)

(b)

3D TISSUE MODEL FORMATION FROM NON-PARALLEL 2D IMAGES

CLAIM OF PRIORITY

This application is a national phase application pursuant to 35 U.S.C. §371 of International Application No. PCT/IB2008/003129, filed May 28, 2008, which claims priority to U.S. Provisional Patent Application No. 60/1940,427 filed on May 28, 2007.

FIELD OF THE INVENTION

We have developed algorithms, designs and methods for a 3D tissue modeling system that can be easily integrated clinically and improves on the range and accuracy of other 2D and 3D systems.

BACKGROUND OF THE INVENTION

Screening techniques for prostate adenocarcinoma (PCa) have increased diagnostic sensitivity to detect early stage diseases. Techniques such as digital rectal exam and prostate-specific antigen (PSA) tests are effective for identifying patients who are at risk; however, these tests cannot definitively diagnose PCa. Biopsy of the prostate is required for a definitive histopathological diagnosis and is usually critical in providing information that allows the prediction of tumor biology and subsequent clinical management.

During the prostate biopsy procedure an "end-firing", 2D transrectal ultrasound (TRUS) probe is inserted into the rectum allowing the prostate to be imaged through the rectal wall (FIGS. 1a and 1b). By rotating the probe, the physician can "fan" through the entire prostate gland and guide the biopsy needle to the desired location(s) (See FIG. 2). Unfortunately, early stage PCa is often isoechoiec and not visible under the conventional ultrasound, or tumor foci are microscopic, so physicians are unable to target tumors directly. Instead, biopsy sites are determined pre-biopsy, based on anatomical zones of the prostate that have a higher probability of harboring PCa. Poor sensitivity (~53%) plagues the prostate biopsy procedure, since tumors are not always targeted directly. Studies have shown PCa detection rates up to 34% on repeat biopsies, after an initial negative biopsy. This inherent inaccuracy may lead to delays in cancer diagnosis and treatment, as well as increased patient anxiety and discomfort due to repeat biopsies.

The current clinical biopsy procedure is confined to using a 2D imaging tool for targeting and recording the 3D biopsy locations. This makes the procedure prone to spatial ambiguity, as the physician tries to envision the 3D location and orientation of their 2D TRUS view within the prostate. This problem is compounded for repeat biopsies, where it is vital that the physician target specific areas in the prostate, either to avoid prior biopsy locations or target them directly—as in the case of lesions, such as atypical small acinar proliferation (ASAP). Repeat biopsies of patients with ASAP in the initial biopsy will result in detection of PCa in 30-50% of cases, with a high probability that the tumor foci is located in the same anatomical region as the ASAP. For these clinical scenarios, the physician's targeting accuracy must be high and consistent, and therefore 3D intra-biopsy prostate information may be essential to increase the detection rate and improve the diagnostic accuracy.

SUMMARY OF THE INVENTION

We have developed a 3D tissue biopsy system that can be easily integrated clinically, by tailoring our implementation in such a way that it requires minimal new hardware and few changes to the current clinical procedure. Constructing a 3D tissue model from a collection of 2D TRUS biopsy images provides the necessary 3D information for intra-biopsy needle guidance and accurate recording of biopsy locations. We have developed a 3D prostate shape reconstruction algorithm that adheres to the restrictions of the current image acquisition device and procedural techniques while requiring minimal new hardware.

DESCRIPTION OF THE INVENTION

Figure 1:
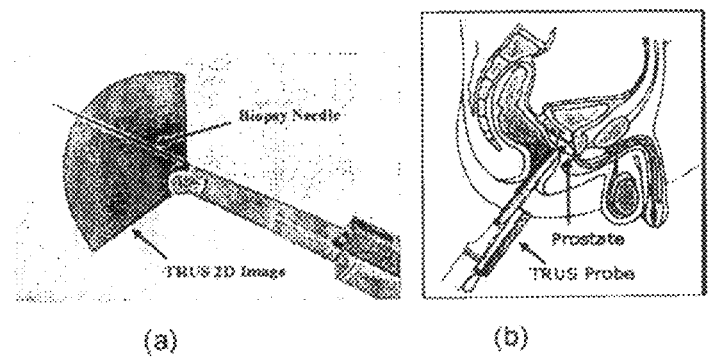
FIG. 1(a) shows a 2D transrectal ultrasound (TRUS) biopsy probe with an attached needle guide. Note: The needle remains within a TRUS scan plane during insertion.
FIG. 1(b) shows the picture of prostate biopsy using a TRUS probe to image the prostate.

The TRUS probe currently used for prostate biopsies is designed with an "end-firing", curvilinear ultrasound transducer, which allows the needle trajectory to remain within the 2D scan field of view during insertion (FIG. 1a). This configuration eliminates the possibility of acquiring parallel biopsy images either in the axial or sagittal planes as the probe is limited to rotational, fan-like movements pivoted around the anus (see FIG. 2). Using this probe, 3D image acquisition would require some form of mechanical assembly, as is done in 3D prostate ultrasound, or would require the physician to complete a continuous sweep of the prostate while the TRUS probe is tracked by a 6 degrees of freedom (DoF) spatial tracking device. The first option would not adhere to current clinical procedure and more importantly would remove the "free-hand" control and range of motion that many physicians prefer. The second option would have little impact on the biopsy procedure; however, to generate a 3D image from a continuous free-hand sweep (or multiple sweeps) would require correcting for prostate deformation caused by the physician inserting and retracting the TRUS probe (leading to vary the pressure on the rectal wall) as they move between the prostate apex and base. The prostate deformation problem can be more directly controlled and minimized by the physician when they are collecting static 2D images as opposed to a continuous 3D scan. Designed around these constraints, our algorithm utilizes a collection of non-parallel 2D biopsy images to effectively reconstruct a patient-specific prostate model.

The inventors have developed a superior system and improved on numerous techniques for 3D prostate model formation from ultrasound images proposed and may be grouped into two general approaches. The first utilizes a form of a 3D deformable shape model to iteratively morph its contour to determine the prostate surface within a 3D US image. While these may be effective techniques for prostate modeling, as stated previously, 3D images are not easily attainable under the current prostate biopsy procedure.

The second group uses a collection of 2D prostate boundaries and carries out some form of surface interpolation or parametric fitting to generate the 3D surface. Tutar et al. used Fourier descriptors to model serial prostate sections. To minimize the number of parameters, cylindrical coordinates were used and a parallel orientation of all 2D prostate image slices was assumed. This assumption fails to adhere to the restrictions of the biopsy probe movement. Furthermore, each of these techniques only incorporates serial prostate slices; however, to accurately model the distal ends of the prostate, it is necessary to utilize data from orthogonal slices. This added information eliminates the dominant variability in shape and volume measurements caused by independent user selection of distal end slices in serial contour sections.

Our innovative method for a 3D prostate model, utilizes an algorithm that involves the collection of 2D TRUS biopsy images, rapid segmentation of the 2D prostate boundary using a deformable contour, followed by 3D surface fitting using radial basis functions (RBFs). Dynamic-deformable contours have been shown to accurately segment the prostate boundary with high precision, while requiring minimal user input. Radial basis functions can effectively interpolate point data generated from a non-standard grid, which would allow for nonparallel TRUS image acquisition. Also, the polyharmonic radial functions have multiple characterizations making them effective for interpolation of disperse data with large information gaps. They have also been used successfully for modeling patient-specific prostheses and vertebrae. Rapid segmentation of the 2D deformable contours combined with the general nature of RBFs make them an ideal combination for 3D prostate model reconstruction from multiple, non-parallel 2D TRUS biopsy images.

As an example, we report on our model reconstruction algorithm tested on simulated 2D TRUS biopsies generated from 3D ultrasound images of real biopsy patients' prostates. The prostate capsule shape and volume accuracy of the reconstructed prostate models are compared to 3D manually segmented prostates, which serve as our "true" prostate model. The accuracy and variability of the reconstruction technique is evaluated as a function of the number of 2D TRUS biopsy images incorporated in the model reconstruction. This indicates the minimum number of biopsy images required to accurately reconstruct a 3D prostate model.

2D Prostate Model Reconstruction

Figure 3:
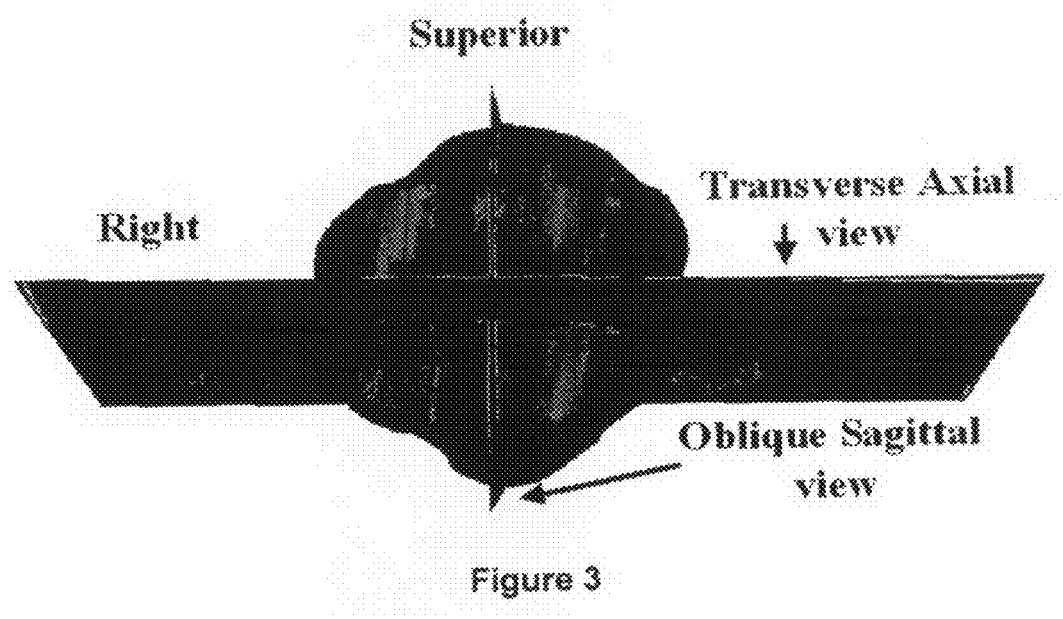
FIG. 3 shows diagram of the two major TRUS imaging planes: transverse axial (seen running horizontally) and oblique sagittal (seen running vertically). The view of the prostate is coronal or in the anterior/posterior direction.

Our proposed prostate model reconstruction algorithm involves acquiring multiple 2D TRUS biopsy images, rapidly segmenting the prostate capsule from the 2D images, and finally fitting a 3D surface using radial basis functions. This technique utilizes prostate biopsy images from transverse axial and oblique sagittal approximately orthogonal views (see FIG. 3). These views are collected and integrated into prostate reconstruction, as together they provide superior estimation of the distal and proximal prostate shape when compared to parallel image acquisition alone.

2.1 Image Acquisition

During the biopsy procedure, but prior to any needle insertions, the physician gathers a representative collection of 2D TRUS images of a patient's prostate. The corresponding 3D position and orientation for each 2D image is recorded using some form of 6 degrees of freedom tracking device (magnetic, optical, etc.) calibrated and attached to the TRUS probe. Images are gathered in both the transverse axial and oblique sagittal (approximately) orthogonal planes (see FIG. 3). It should be noted that, within the current clinical biopsy procedure, image acquisition could easily be performed during a 5-10 minute patient exploratory time that occurs prior to any needle insertion.

2.2 2D Boundary Segmentation

Along with image acquisition, the prostate boundary in each 2D image is segmented using the semi-automated segmentation technique described by Ladak et al. (U.S. Pat. No. 6,778,690). This technique uses a dynamic deformable contour (DDC) to rapidly fit the prostate boundary from a 2D ultrasound image. The DDC was chosen because it requires the minimal user interaction since only 4-6 user-defined prostate boundary points are necessary to generate a 2D contour with a boundary accuracy greater than 95%.

The DDC is iteratively deformed by dynamically moving each vertex, Vi, according to its force calculation:

$$f_i^{tot} = w_i^{int} f_i^{int} + w_i^{img} f_i^{img} + w_i^d v_i \qquad (1)$$

where $f_i^{int}$ is the internal or curvature force to maintain contour smoothness, $f_i^{img}$ is the image or external force used to drive contour an edge, and vi is the damping force based on the vertex velocity, and $w_i^{int}$, $w_i^{img}{}_i$, and $w_i^d$ are weighting parameters, which as an example can be set to be $w_i^{int}$=0.3, $w_i^{img}{}_i$=1.0, $w_i^d$=−0.5, as recommended in.

2.3 3D Model Reconstruction

Once the 2D prostate boundaries are collected from both orthogonal orientations, a 3D prostate surface is fitted using radial basis functions (RBFs). RBFs are an effective interpolation approach that has been used in a variety of medical and non-medical applications.

RBFs are well suited for our biopsy application as they do not restrict input boundary points to lie within a regular grid, which is not feasible for free-hand TRUS image collection. Also, the variable characterization of polyharmonic RBFs is extremely effective at interpolating large "data-free" gaps within the input model, which make RBFs ideal for interpolating a sparse collection of TRUS biopsy images. Biharmonic splines were used as the basic function, which has been shown to be the smoothest interpolant.

Interpolation using RBFs uses a function s: $R^3 \to R$ that approximates the input function f: $R^3 \to R$, where {f(xi): i=1, 2, ..., n} represents the set of input prostate boundary points. For our application, the surface approximation, s(x), is of the form:

$$s(x) = p_1(x) + \sum_{i=1}^{n} \lambda_i \phi(\|x - x_i\|), x \in \mathbb{R}^3; \lambda_i \in \mathbb{R} \qquad (2)$$

where p1 is a first order polynomial, |●| represents the Euclidean norm, and φ(r)=r for biharmonic splines. As a side note, the inputs xi are often referred to as "radial centers". The coefficients, λi, are determined by requiring that s satisfy the interpolation condition:

$$s(xi) = f(xi), i = 1, 2, \ldots, n \qquad (3)$$

as well as the side conditions:

$$\sum_{j=1}^{n} \lambda_j q(x_i) = 0, \text{ for all } q \in \pi_1^3 \qquad (4)$$

where $\pi_1^3$ represents all 3-variable, first-order polynomials.

In the case of noisy input data (as could be caused by poor 2D prostate segmentations or noise in tracking the TRUS probe), spline smoothing of s(x) may be done by minimizing:

$$\rho\|s\|^2 + \frac{1}{n}\sum_{i=1}^{n}(s(x_i) - f(x_i))^2 \qquad (5)$$

where ρ is an input smoothing constant $\geq$0 and $|s|^2$ is a measure of the energy in the second derivative of s. This affects equation 3 by:

$$s(xi) = f(xi) + \rho \lambda i, i = 1, 2, \ldots, n \qquad (6)$$

As an example ρ=5 was heuristically selected for prostate model reconstruction when noise was added to the TRUS image position (as described in section 3.4).

Once the RBF, s(x), has been estimated, then a simple iso-surfacing technique is used to generate the patient's 3D prostate model.

3 Experimental Methods

To test the efficacy of our reconstruction algorithm, we used 3D TRUS images, obtained from patients prior to prostate biopsies, to extract 2D images, which were used to simulate real 2D TRUS biopsy images. It is advantageous to use simulated 2D biopsy images in place of 2D images obtained during the biopsy procedure, because the "true" 3D prostate volume and shape can be calculated from the original 3D TRUS image and is perfectly matched with the simulated data. As a result, the 3D prostate information can be used to quantify the accuracy and variability of our reconstruction model. All simulated biopsy TRUS images were examined by an expert radiologist and urologist to ensure that the 2D TRUS images used in our evaluation resembled TRUS images obtained during the biopsy procedure.

3.1 Patient Data Acquisition

To demonstrate our model reconstruction technique, we obtained 3D US images (voxel dimensions of 0.154×0.154× 0.154 mm$^3$) of 10 patients' prostates using a "side-firing", linear array TRUS probe mounted on a rotational mover. The "side-firing" TRUS probe is different from the "end-firing" TRUS probe (FIG. 1a) used in the prostate biopsy procedure, and the mechanized rotational system makes this system not sensible for the current clinical biopsy procedure. All patients were clinically selected to undergo the prostate biopsy procedure and were of mean age 69.6±9.1 years. The prostate volumes ranged from 22 cm$^3$ to 70 cm$^3$, with an average size of 47.8±12.9 cm$^3$, as typically found at the time of biopsy.

A 3D model of each patient's prostate, which was used as our "true" boundary, was generated from the 3D prostate images using the radial reslicing method and manual segmentation as described by Wang et al. In this technique, 60 2D prostate boundary segmentations were completed at a radial reslicing angle of 3° about the anterior/posterior axis through the center of the prostate. This method was selected over parallel step planimetry because of its superior estimation of the volume and capsule boundary at either end of the prostate. The 3D planimetry prostate models were considered our "truth" models for prostate capsule boundary and volume comparison.

3.2 Biopsy Simulation

Figure 2:
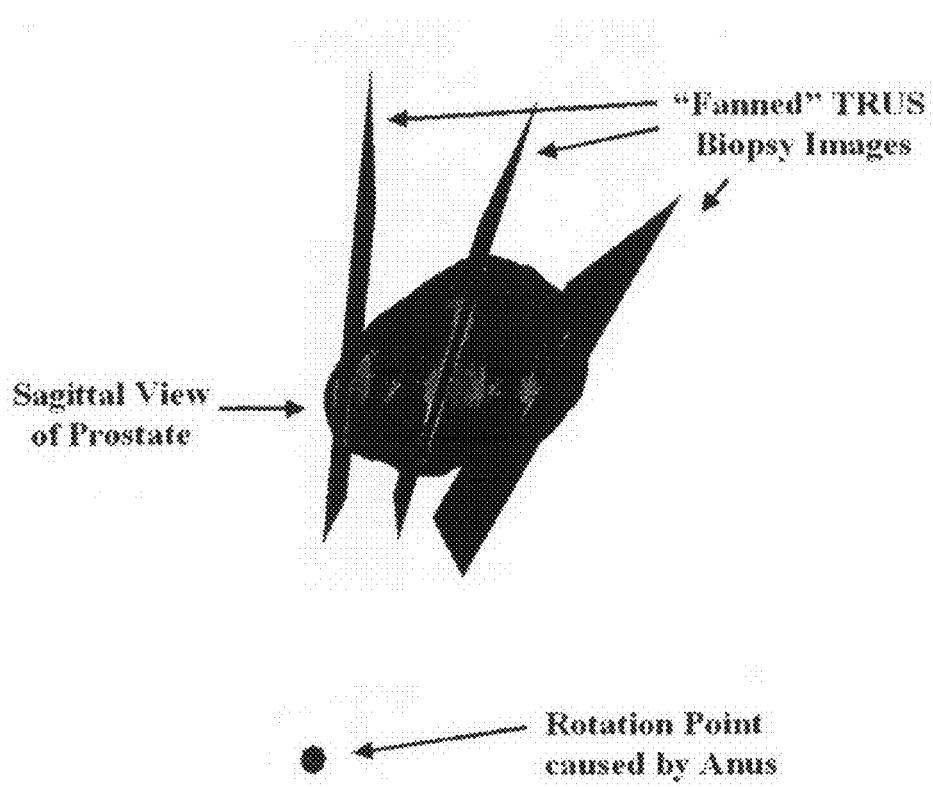
FIG. 2 shows illustration of the "fanned" nature of TRUS image collection caused by rotating the TRUS probe around the anus (see FIG. 1b). Transverse axial TRUS images shown (see FIG. 3) and prostate view is in the sagittal direction.

2D TRUS image slices were extracted from the 3D US patient images using a fanned rotation about an off-image point assumed to be equivalent to the rotational pivot formed by the anus (FIG. 2). Since the 2D TRUS biopsy probe is end-firing (FIG. 1a), the fulcrum formed by the anus dictates the angle at which the 2D TRUS biopsy probe is positioned and the corresponding orientation of the acquired biopsy image.

In the simulation, the point of rotation was placed 3.9 cm from the prostate apex to match the normal anatomical distance from the prostate to the anus. The angle formed between the 3D TRUS prostate image and rotation point was selected heuristically, with aid of an expert radiologist, by observing the 2D TRUS image formed at different angles.

After the rotation point was determined, fanned acquisition of 2D TRUS images was completed in both the transverse axial and oblique sagittal views. 11 transverse axial and 7 oblique sagittal 2D prostate images, spanning the prostate, were generated for each patient. The angle of rotation between consecutive slices was constant for each individual acquisition sweep and was determined based on user-defined, arbitrarily selected rotational start and end points for each patient's prostate (FIG. 2). Because the start and end points were selected independently for each patient, angles between consecutive slices were not constant across patients, which is desirable to limit any effect of reconstruction bias related to structured angle orientations. In general, the inter-slice angles were between 2°-3° in the transverse axial direction and 4.5°-5.5° in the sagittal direction. This corresponds to approximately 1.4-2.0 mm and 3.1-3.8 mm distance between slices at the posterior edge of the prostate (the edge adjacent to the rectal wall) for the transverse axial and sagittal views respectively. Labeling of the 2D biopsy images was consistent across all patients. Transverse images were labeled 1-11 starting from the prostate apex moving towards the prostate base, and sagittal images were labeled 1-7 moving from right to left across the prostate.

3.3 Model Formation

After the 2D TRUS biopsy images were simulated, each patient's prostate data was composed of 7 sagittal and 11 transverse axial images. These images were used in the model reconstruction algorithm (described in sec. 2) to generate each patient's 3D prostate models. Multiple prostate models were reconstructed for each patient by varying the total number of sagittal and transverse axial biopsy images used in the model reconstruction. This was done to examine how the accuracy of our reconstructed prostate models varied as the prostate boundary information was increased. The number of images used in reconstruction varied from 1 sagittal, 2 axial TRUS images to 7 sagittal, 7 axial images. Also, the specific combination of 2D biopsy images used for reconstruction was varied for a given number of s sagittal and t transverse images such that, for patient i, a set of prostate volumes, Vs, t, i=[vs,t,i]$_m$ was formed, where m represents the number of prostate volumes reconstructed using different combinations of s sagittal and t transverse axial 2D biopsy images. Table 1 outlines the different groups of image combinations and number of volumes calculated within each group.

3.4 Orientation and Position Noise

Noise was added to the orientation and position information for each simulated 2D TRUS biopsy image to better replicate results that could be expected from obtaining tracked 2D TRUS images. Noise in the image location is caused by errors in the 6 DoF tracking device used to localize the 2D TRUS images in 3D. Due to the nature of the prostate biopsy procedure, it was assumed that tracking of the probe would be done at a marker on the handle end of the TRUS probe, which is external to the patient's body and is about 25-30 cm from the ultrasound transducer. This distance has significant implication to the TRUS image localization as any errors in tracking the marker angulation off of the probe axis results in both angulation and position errors for the TRUS image.

To model appropriate noise for our simulated biopsy images, we used a Gaussian random number generator to build translational errors in the x,y,z direction, $\epsilon x$, $\epsilon y$, $\epsilon z$, as well as a rotational error, $\epsilon_\theta$, rotated about a random vector in $R^3$. This generated noise was applied to "virtual marker" locations for each simulated 2D TRUS biopsy image, which was then used to calculate the appropriate noisy image transform. Noise was generated independently for each simulated 2D TRUS biopsy image and was assumed to be Gaussian and uniformly distributed around the true marker location (ie. $\mu=0$). Standard deviation values for the Gaussian random number generator were set at 0.3 mm for each translational axis and 0.5° for angulation error. These values are conservative estimates of the upper boundary for optical and magnetic tracking systems (Wiles et al., 2004; Tang and Cleary, 2003; Corral et al., 2003). The "virtual marker" to TRUS image distance was set at 28.5 cm, which corresponds to an ergonomically reasonable marker location on a conventional ATL C9-5 TRUS biopsy probe (Philips Medical Systems, Seattle, Wash.). This noise generation was run 10 times for each patient, which produced 10 sets of noisy locations of the 2D TRUS biopsy images for each patient.

3.5 Evaluation

The accuracy of our 3D prostate reconstruction was demonstrated for all 10 patients using volume- and shape-based metrics to compare each patient's reconstructed 3D models with their "true" prostate model obtained from the original 3D TRUS images. These metrics provide localized, regional information on prostate surface errors as well as a demonstration of our volume measurements.

3.5.1 Volume-Based Metrics

Volume based metrics assess the global accuracy of the reconstructed model's volume compared to the "true" volume. These values are clinically important as prostate cancer therapies are directed or modified based on the volume of the gland.

(1) Volume Error, VE(V,V*), described in equation 7, is used to calculate the signed volume error of a reconstructed

TABLE 1

List of the different sets of sagittal and transverse axial TRUS biopsy images used for prostate model reconstruction, as well as the number unique combinations produced for each set.

| | # biopsy images | | | | | | | | | |
|---|---|---|---|---|---|---|---|---|---|---|
| | 3 | 4 | 5 | 6 | 7 | 9 | 10 | 11 | 12 | 14 |
| (sagittal, transverse) | (1, 2) | (2, 2) | (2, 3) | (3, 3) | (4, 3) | (4, 5) | (5, 5) | (4, 7) | (7, 5) | (7, 7) |
| # of Combinations | 20 | 40 | 20 | 10 | 20 | 13 | 10 | 12 | 5 | 8 | prostate volume, V, compared to the gold standard, V* as a percentage of the "true" volume.

$$VE(V, V^*) = \frac{V - V^*}{V^*} \times 100\% \quad (7)$$

(2) Absolute Volume Error, AVE(V,V*), described in equation 8, is used to calculate the absolute volume error of a reconstructed prostate volume, V, compared to the gold standard, V*, as a percentage of the "true" volume.

$$AVE(V, V^*) = \frac{|V - V^*|}{V^*} \times 100\% \quad (8)$$

where |•| represents the absolute scalar value.

(3) Sensitivity, S(V,V*), described in equation 9, is used to calculate the proportion of the reconstructed prostate volume, V, that is correctly overlapped with the "true" volume, V*.

$$S(V, V^*) = \frac{TPV}{V^*} \times 100\% \quad (9)$$

where the true positive volume, TPV, represents the "correctly" overlapped volume of the models, such that TPV=V∩V*.

(4) Difference (or error), Df(V,V*), described in equation 10, is used to calculate the proportion of the volume that is not correctly overlapped with the gold standard volume, V*.

$$Df(V, V^*) = \frac{FPV + FNV}{V^*} \times 100\% \quad (10)$$

where FPV=V−TPV and FNV=V*−TPV, represent the false positive volume and false negative volume, respectively.

3.5.2 Shape-Based Metrics

Shape Based metrics evaluate the local contour shape of reconstructed prostate models by comparing the surface distances between a reconstructed model and the "truth" model. These metrics demonstrate how closely a reconstructed model represents the patient-specific prostate shape.

The distance between two prostate surfaces was calculated using a modified implementation of the symmetric Hausdorff distance calculation. In these calculations, both the reconstructed prostate model surface and the "true" 3D model are symbolically viewed as continuous surfaces, S and S* respectively. The Euclidean surface error can be determined for each point p∈S, by calculating the minimum distance to the surface S*:

$$d(p, S^*) = \min_{p^* \in S^*} |p - p^*| \quad (11)$$

where |•| denotes the vector norm. The signed surface error can then be determined by adding an inside(−)/outside(+) function to equation (11):

$$d(p, S^*, c) = \lfloor (p - p^*_{min}) \cdot (p - c) \rfloor \times d(p, S^*) \quad (12)$$

where c represents the reconstructed prostate model centroid and $[p - p^*_{min} \cdot (p-c)]$ uses the vector dot-product to determine the location of the reconstructed model point relative to the "truth" model surface.

Figure 4:
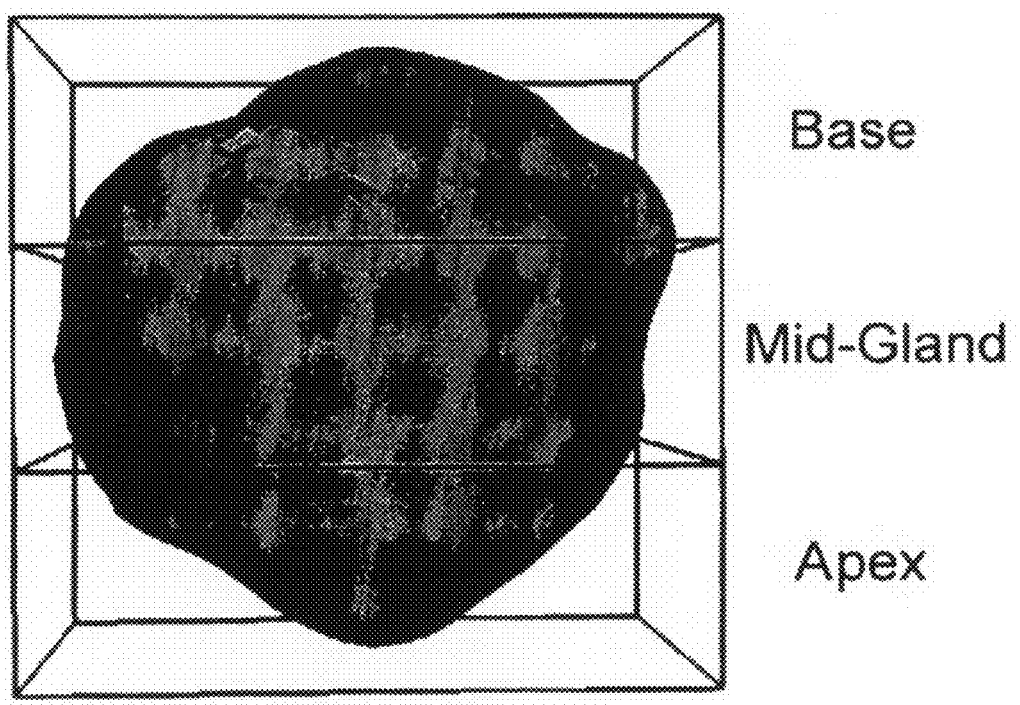
FIG. 4 shows illustration of approximate clinical prostate regions along the inferior/superior axis. The view of the prostate is coronal or in the anterior/posterior direction.

Unlike volumetric measurements, distance measures are locally computed and 18, and therefore, allow for both global and regional valuation of prostate shape within each of the metrics. To evaluate significant anatomical regions independently, we divided the prostates into three equal regions along the axial axis (see FIG. 4). These regions correspond to the approximate prostate base, mid-gland and apex, which are the three regions targeted separately in the clinical sextant biopsy method.

The shaped-based metrics used are as follows:

(1) Mean Distance Error, MD(R,S*,c), described in equation 13, is used to calculate the mean of the signed distances (equation 12) from a region of the reconstructed prostate surface, {R: R⊆S}, to the "true" surface, S*.

$$MD(R, S^*, c) = \frac{\sum_{p \in R} d_s(p, S^*, c)}{\text{surface\_area}(R)} \quad (13)$$

(2) Mean Absolute Distance Error, MAD(R,S*), described in equation 14, is used to calculate the mean of the distance error (equation 11) from all points within a region of the reconstructed prostate surface, {R: R⊆S}, to the corresponding nearest point on the "true" surface, S*.

$$MAD(R, S^*) = \frac{\sum_{p \in R} d_s(p, S^*)}{\text{surface\_area}(R)} \quad (14)$$

3.5.3 Mean Metric Evaluation

As described Section 3.3, a set of prostate volumes, Vs, t, i, is defined as the set of size m of all unique prostate volumes for patient i that incorporate s 2D sagittal images and t 2D transverse images for model formation. Therefore, s,t,i (j)=vs,t,i,j; 0<j≦m, where vs,t,i,j represents a specific combination of s sagittal and t transverse images and m is the total number of different combinations for s sagittal and t transverse images. For a particular metric, f(v,g), where v represents a reconstructed model and g represents the patient's corresponding "truth" model, the mean and variance were calculated for each combination of sagittal and transverse images.

$$\mu_{s,t}(i) = \frac{\sum_{j=1}^{m} f(V_{s,t,i}(j), g_i)}{m} \quad (15)$$

$$\sigma^2_{s,t}(i) = \frac{\sum_{j=1}^{m} (f(V_{s,t,i}(j), g_i) - \mu_{s,t}(i))^2}{(m-1)^2}$$

This provides an estimation of the intra-patient accuracy and variability for different combinations of sagittal and transverse images. To examine inter-patient statistics, the global mean and deviation was calculated across all i patients:

$$M_{s,t} = \frac{\sum_{i=1}^{n} \mu_{s,t}(i)}{n}$$

$$S_{s,t}^2 = \frac{\sum_{i=1}^{n} (\mu_{s,t}(i) - M_{s,t})^2}{n-1}$$

3.5.4 Noise Evaluation

To evaluate our tolerance to noise, similar equations were used as above, except in equation (15), $V_{s,t,i}(j)$ is substituted with the mean metric value for all noise iterations, $k = 1, 2, \ldots K$, such that:

$$\mu_{s,t}(i) = \frac{\sum_{j=1}^{m} \mu_{s,t,i}^*(j)}{m}$$

$$\sigma_{s,t}^2(i) = \frac{\sum_{j=1}^{m} (\mu_{s,t,i}^*(j) - \mu_{s,t}(i))^2}{(m-1)^2}$$

where $$\mu_{s,t,i}^*(j) = \frac{\sum_{k=1}^{K} f(V_{s,t,i,j}(k), g_i)}{K}$$

$$\sigma_{s,t,i}^{*2}(j) = \frac{\sum_{k=1}^{K} (f(V_{s,t,i,j}(k), g_i) - \mu_{s,t,i}^*(j))}{(k-1)^2}$$

4 Results

Figure 5:
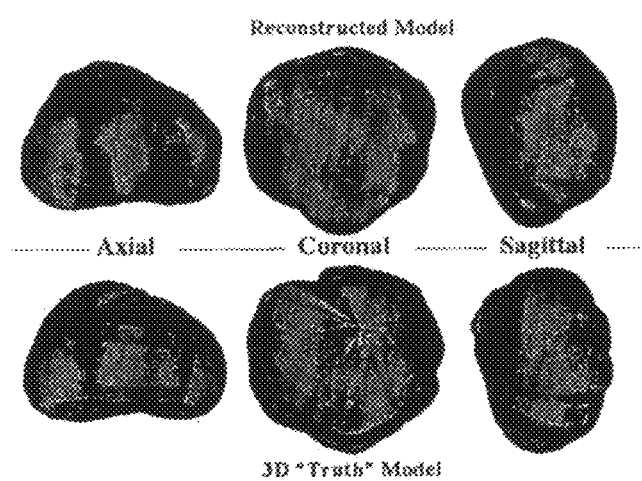
FIG. 5 shows comparison of orthogonal views of a reconstructed prostate model (top), using 7 sagittal and 7 transverse biopsy images, and the patient's corresponding 3D "true" model (bottom)
Figure 6:
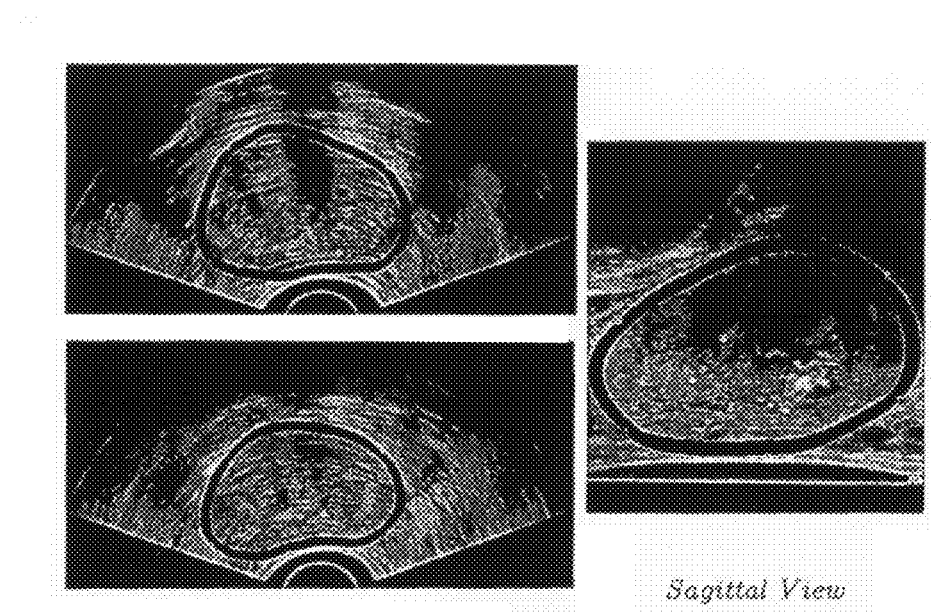
FIG. 6 shows axial and sagittal views of a patient's reconstructed prostate—reconstructed from 4 sagittal and 3 transverse TRUS biopsy images—overlayed on arbitrary cross-sections of the original 3D TRUS image. Note: The 2D cross-sections shown above do not correspond to the 2D TRUS images used for model reconstruction.

Qualitative examination of our reconstructed 3D prostate models demonstrate our 3D reconstruction algorithm is capable of capturing the 3D surface topology of each patient's prostate (example see FIG. 5). As expected, 3D models formed from an increased number of 2D prostate boundaries better characterize the prostate capsule shape and aberrations in the reconstructed prostate surface; however, with as few as 6-7 2D TRUS images, a reasonable estimation of the prostate surface can be obtained, demonstrating the increased efficiency of the 3D system. When we overlayed a patient's 3D prostate model on their original 3D prostate image, there was strong agreement between the prostate model and the TRUS image prostate boundary. This held true for cross-sections not aligned with any of the 2D slices used for model reconstruction (FIG. 6).

4.1 Volume-Based Metric Results

Figure 7:
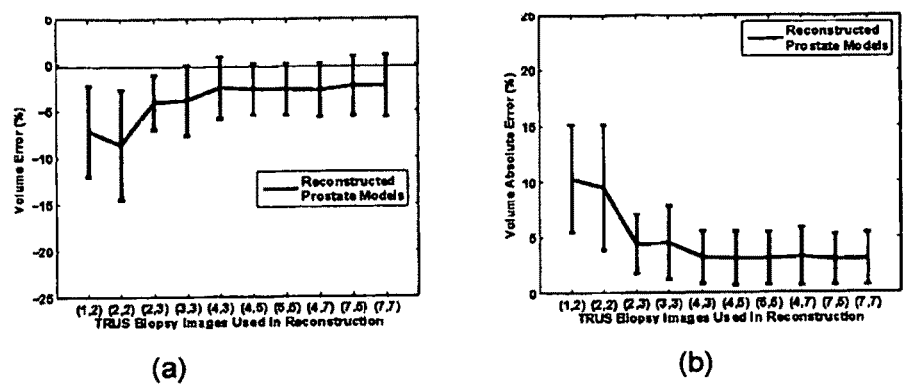
FIG. 7(a) shows plots of the mean signed volume error, VE(V,V*) (see eqn. 7), for all 10 patient's reconstructed prostates.
FIG. 7(b) shows plots of the mean absolute volume error, AVE(V,V*) (see eqn. 8), for all 10 patients. The horizontal axis indicates the number of 2D TRUS biopsy images used in model reconstruction (# of sagittalimages, # of transverse axial images). Error bars represent 1 standard deviation of the means.

The mean results of our volume and shape-based metrics (section 3.5.1 & 3.5.2 respectively) across all 10 patients, as outlined in section 3.5.3, provide a quantitative evaluation of both the accuracy of the prostate shape and volume across a range of prostate shapes and sizes. FIG. 7 shows plots of both the signed volume error, VE(V,V*), (FIG. 7a) and absolute volume error, AVE(V,V*), (FIG. 7b). The volume error values are plotted in ascending order according to the number of 2D TRUS images used in reconstruction. Both the mean volume error and mean absolute volume error decreased as more 2D TRUS images were incorporated into the model reconstruction before appearing to plateau at about 7 TRUS images (4 sagittal and 3 transverse axial), where the mean volume error and absolute volume error were −2.4±3.3%

Figure 8:
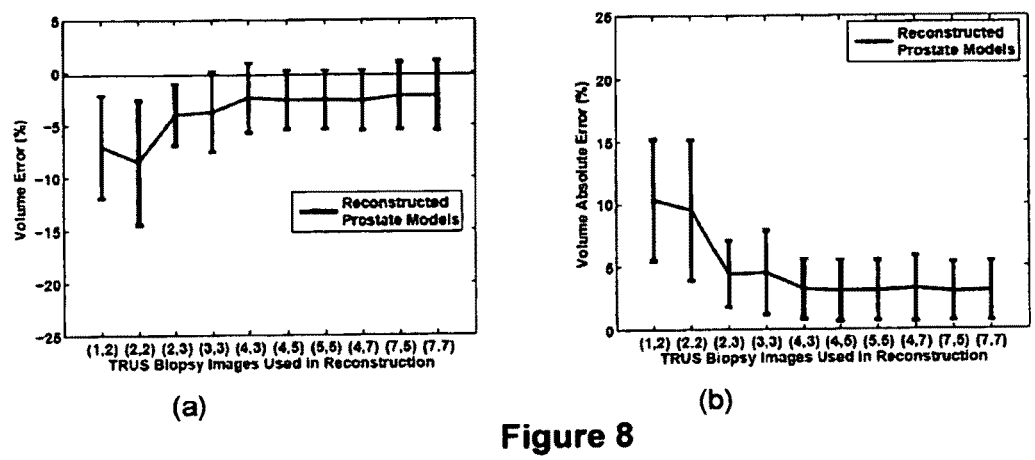
FIG. 8(a) shows plots of the mean overlapped volume sensitivity, S(V,V*), for all 10 patient's reconstructed prostates.
FIG. 8(b) shows plots of the mean overlapped volume difference, Df(V,V*) (see eqn. 10), for all 10 patients. The horizontal axis indicates the number of 2D TRUS biopsy images used in the model reconstruction (# of sagittal images, # of transverse axial images). Error bars represent 1 standard deviation of the means.

FIG. 8 shows how accurately the reconstructed prostate model's volume overlaps with the true prostate volume, S(V, V*), (FIG. 8a from equation 9) and to what fraction they differ in volume, Df(V,V*), (FIG. 8b from equation 10). The independent variable within the plots is organized in ascending order according to the number of 2D TRUS images used in model reconstruction. FIG. 8a shows that on average with as few as 5 TRUS biopsy images (2 sagittal, 3 transverse axial), over 90% of a patient's true prostate volume is contained within the reconstructed prostate model. The volumetric difference error between the reconstructed prostate models and "true" prostate (FIG. 8b) fell within 15% quickly and then plateaued around 12%. The volume sensitivity was 0.93±0.02 and the volume difference was 0.12±0.01 for 4 sagittal and 3 transverse images, which for both plots was on the plateau of the mean curves.

4.2 Shape-Based Metric Results

Figure 9:
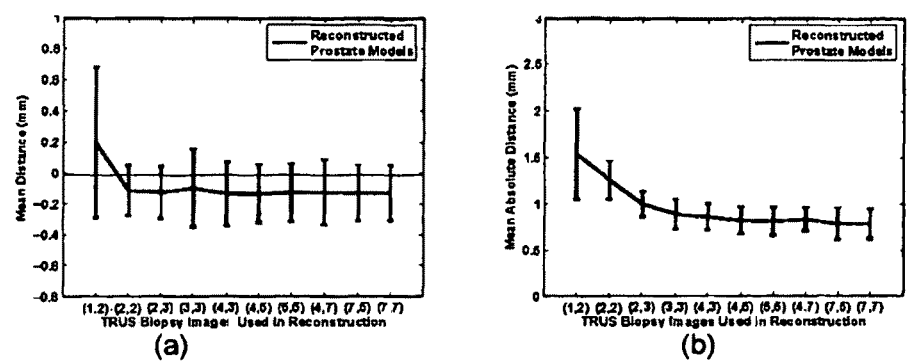
FIG. 9(a) shows plots of the mean signed distance error, MD(R,S*,c, across the entire prostate (ie. R=S), averaged over all 10 patients.
FIG. 9(b) shows plots of the mean unsigned distance error, MAD(R,S*), across the entire prostate (ie. R=S), averaged over all 10 patients. The horizontal axis indicates the number of 2D TRUS biopsy images used in the model reconstruction (# of sagittal images, # of transverse axial images). Error bars represent 1 standard deviation of the means.

FIG. 9 shows the plots measuring the mean signed distance, MD(V,V*), and the mean unsigned (absolute) surface distance error, MAD(V,V*), as outlined in equations 13 and 14 respectively. Similar to what was seen in FIG. 7, the general decrease in the boundary error appears to reach a point of diminishing returns at about 7 TRUS images where MD(V,V*)=−0.13±0.21 mm and MAD(V,V*)=0.87±0.14 mm.

Figure 10:
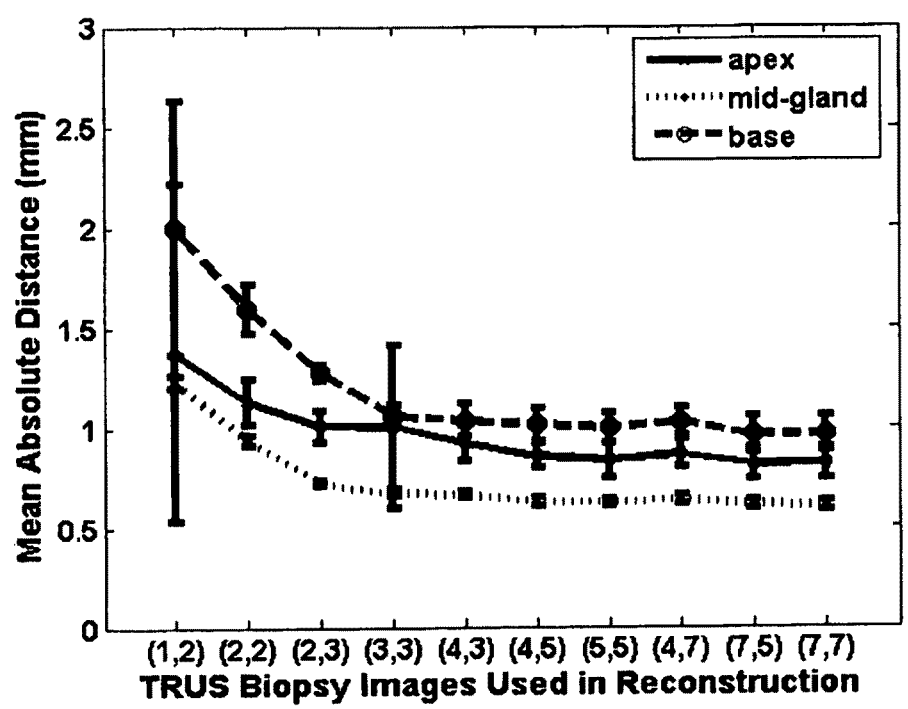
FIG. 10 shows plots of the mean unsigned prostate surface boundary error, MAD(R,S*) (see eqn. 14), for each of the 3 clinical prostate regions (see FIG. 4), averaged over all 10 patients. The horizontal axis indicates the number of 2D TRUS biopsy images used in the model reconstruction (# of sagittal images, # of transverse axial images). Error bars represent 1 standard deviation of the means.

When the reconstructed prostates were split into their three clinical regions—apex, mid-gland, and base (see FIG. 4), the mean unsigned surface error showed the greatest error in the prostate base, followed by the apex (see FIG. 10). Further evaluation showed that the anterior portion of the prostate base was the least accurate sector.

4.3 Noise Results

Figure 11:
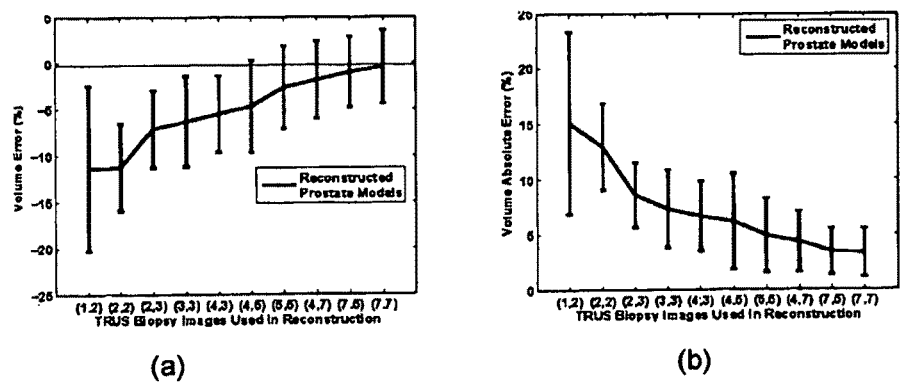
FIG. 11(a) shows plots of the mean signed volume error, VE(V,V*), for all 10 patient's reconstructed prostates with noise added.
FIG. 11(b) shows plot of the mean absolute volume error, AVE(V,V*), for all 10 patients with noise added. The horizontal axis indicates the number of 2D TRUS biopsy images used in the model reconstruction (# of sagittal images, # of transverse axial images). Error bars represent 1 standard deviation of the means.
Figure 12:
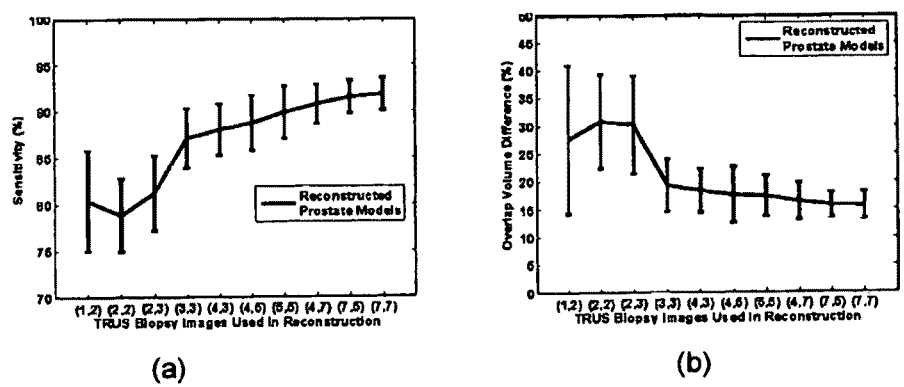
FIG. 12(a) shows plots of the mean overlapped volume sensitivity, S(V,V*), for all 10 patient's reconstructed prostates with noise added.
FIG. 12(b) shows plots of the mean overlapped volume difference, Df(V,V*), for all 10 patients with noise added. The horizontal axis indicates the number of 2D TRUS biopsy images used in model reconstruction (# of sagittal images, # of transverse axial images). Error bars represent 1 standard deviation of the means.

The addition of noise into the 3D position and orientation information of the 2D biopsy images led to a general increase in a both volume and shape based error for the 10 patients' reconstructed prostate models. Once again, the general trend in all of the mean curves (FIGS. 11, 12,13) was toward decreasing the error as additional prostate boundary images were added. The mean volume error, VE(V,V*), plot (FIG. 11a) still displayed a systematic underestimation of the prostate volume as was seen in FIG. 7a. The mean absolute volume error, AVE(V,V*), (FIG. 7b) generally increased with the introduction of noise as the volume error for 7 TRUS images (4 sagittal and 3 transverse axial) was 6.7±3.2% as compared to 3.2±2.4% that was observed in the noise-free testing.

The overlapped volume calculations showed a drop in the sensitivity, S(V,V*), (compared to the noiseless version) with a plateau at about 90% (FIG. 12a) and an increase in the volume difference, Df(V,V*), to a plateau at about 15% (FIG. 12b). The values at 4 sagittal, 3 transverse biopsy images generally deteriorated with the introduction of noise from S(V,V*)=0.93±0.02 and Df(V,V*)=0.12±0.01 in the case with no noise to S(V,V)=0.88±0.03 and Df(V,V*)=0.18±0.04 in the case with noise.

Figure 13:
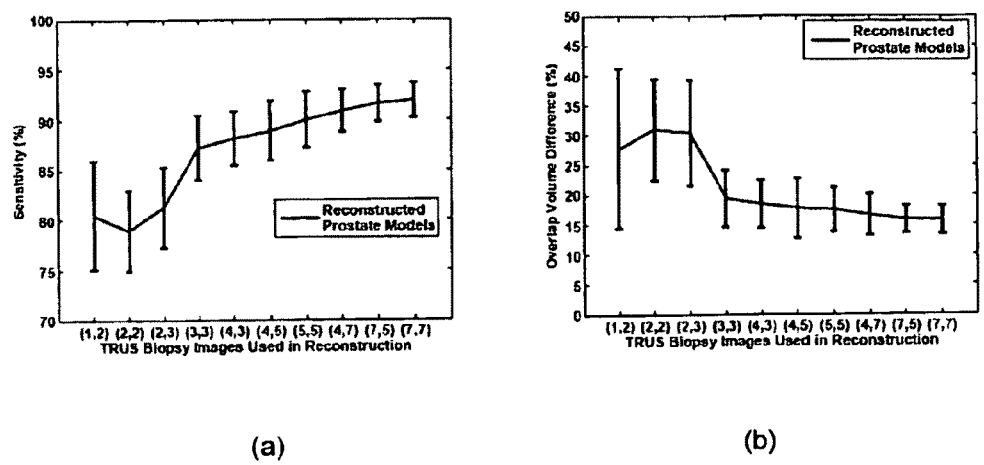
FIG. 13(a) shows noise plots of the mean signed distance error, MD(R,S*,c), averaged over all 10 patients with noise added.
FIG. 13(b) shows plots of mean unsigned distance error, MAD(R,S*) (see eqn. 14), averaged over all 10 patients with noise added. The horizontal axis indicates the number of 2D TRUS biopsy images used in the model reconstruction (# of sagittal images, # of transverse axial images). Error bars represent 1 standard deviation of the means.

FIG. 13 shows the signed and unsigned distance errors of the reconstructed prostate models after the introduction of noise to the data. The signed distance error plot (FIG. 13a) shows little change in the mean values from the case without noise (FIG. 9a), except for an increase in the standard deviation values. There is a general increase in the unsigned mean boundary error (FIG. 13b), with a plateau at about a 1.3 mm error for 7 TRUS images used in the model reconstruction. The signed and unsigned mean boundary errors at 4 sagittal, 3 transverse biopsy images increased to −0.20±0.25 mm and 1.34±0.20 mm from the case without noise of −0.13±0.21 mm and 0.87±0.14 mm, respectively.

Our results demonstrate that with as few as seven 2D TRUS biopsy images (4 sagittal and 3 transverse), a reasonable 3D model of a patient's prostate can be made with an average mean unsigned prostate surface boundary error of 0.87±0.14 mm and volume error of −2.4±3.3% in the ideal case without noise and 1.34±0.20 mm and −5.3±4.1% with the introduction of noise. The inclusion of more than 7 TRUS images does not appear to provide a significant improvement in estimating the prostate volume and shape using our reconstruction methods. Using fewer than 7 TRUS images (such as 3 sagittal and 3 transverse) appears to destabilize the consistency of the reconstruction algorithm, resulting in a prostate model with greater volume and shape variability across patients.

Overall, the absolute surface boundary errors were on average less than 1.5 mm, for the minimum of 7 TRUS biopsy images, even with the addition of noise. This value is clinically acceptable as the common diameter of a prostate biopsy needle is 2 mm. Our signed distance and volume measurement also showed a bias in our model reconstruction algorithm toward underestimation of the prostate boundary. This underestimation likely occurs because significant interpolation is required to fill the data gaps between our sparsely sampled set of 2D TRUS prostate images. As a result, rapid changes in topology are not captured as well and likely lead to these inaccuracies.

As we would expect, when the prostate is broken down into its different clinical regions, we see that areas of high curvatures (prostate base and apex) have a higher level of an boundary error compared to those with more gradual change (mid-gland). The greatest boundary errors appear concentrated in the anterior portion of the gland base, which is at the interface of the prostate with the bladder. This interface lies primarily within the transition zone of the prostate. Interestingly, the transition zone has a significantly lower incidence of PCa. To improve the overall model accuracy in this region (and for the prostate overall), it would be optimal to either increase the number of transverse axial TRUS biopsy images collected from the base region or increase the number of mid-sagittal images, to ensure that the rapid change in surface topology in the anterior base region could be accurately modeled.

From a clinical utility perspective, six to seven 2D TRUS images are currently collected (for medical and legal record) as part of a regular biopsy procedure. Reconstruction of the prostate model from seven 2D TRUS images would likely only add an addition 1-2 minutes, most of which would be setting the seed-points for the semi-automatic segmentation of the prostate boundary from the 2D images. This could fit easily within the 5-10 min clinical patient workup prior to any needle insertion. The number of 2D TRUS images collected could also be increased for patient's with irregular prostate shapes involving an extensive curvature; however, our results suggest that for most prostates, 7 TRUS images appear to be the ideal number when comparing the increased procedural time vs. model accuracy trade off. Developing an accurate, completely automated 2D prostate segmentation technique would reduce the procedural time cost for prostate model reconstruction and would also allow for additional 2D TRUS images to be used in model reconstruction.

We have proposed and tested a 3D prostate model reconstruction algorithm that is capable of accurately reconstructing a patient-specific prostate from a sparse collection of non-parallel, sagittal and axial 2D TRUS biopsy images.

The 3D prostate model reconstruction system is as follows:

A) A novel system including methodology, design and algorithms for 3D Tissue Model Formation using Parallel or Non-Parallel 2D images.

B) Use of the above Tissue Model Formation a per A) for use in modeling the Prostate C) Use of the Prostate Model Formation as per B) for use with Biopsy Images for surgical and biopsy implementation, recording, tracking, and planning.

D) Use of the above Tissue Model Formation as per A) for use in Kidney, Vasculature, Brain, and Tumor.

What is claimed is:

1. A method for reconstructing a three dimensional model of an object, comprising the steps of:
   receiving a plurality of two dimensional images;
   segmenting a two dimensional object boundary in each of the two dimensional images, wherein the two dimensional object boundary in each of the two dimensional images is segmented using a deformable contour; and
   performing three dimensional fitting of the segmented two dimensional object boundaries using a radial basis function.

2. The method according to claim 1, wherein the plurality of two dimensional images are ultrasound images.

3. The method according to claim 1, wherein the plurality of two dimensional images are transrectal ultrasound (TRUS) images.

4. The method according to claim 3, wherein the TRUS images are formed from signals obtained by a two dimensional TRUS probe.

5. The method according to claim 4, wherein the two dimensional TRUS probe is mounted on a rotational mover.

6. The method according to claim 1, wherein a three dimensional position and an orientation of each of the plurality of two dimensional images are recorded.

7. The method according to claim 1, wherein the plurality of two dimensional images are in transverse axial planes or oblique sagittal and approximately orthogonal planes.

8. The method according to claim 1, wherein the deformable contour is a dynamic deformable contour.

9. The method according to claim 8, wherein the dynamic deformable contour is obtained by dynamically moving each vertex which satisfies a first equation, $f_i^{tot} = w_i^{int} f_i^{int} + w_i^{img} f_i^{img} + w_i^d v_i$ wherein $f_i^{int}$ is an internal or curvature force to maintain contour smoothness, $f_i^{img}$ is an image or external force used to drive contour an edge, $v_i$ is a damping force based on a vertex velocity, and $w_i^{int}$, $w_i^{img}$, and $w_i^d$ are weighting parameters.

10. The method according to claim 1, wherein the step of performing three dimensional fitting using a radial basis function comprises the step of interpolating the segmented two dimensional object boundaries in the plurality of two dimensional images using the radial basis function.

11. The method according to claim 10,
    wherein the segmented two dimensional object boundaries in the plurality of two dimensional images are interpolated according to a second equation, $$s(x) = p_1(x) + \sum_{i=1}^{n} \lambda_i \phi(\|x - x_i\|), x \in \mathbb{R}^3, \lambda_i \in \mathbb{R}$$

where $s(x)$ is surface approximation of the object, $p_1$ is a first order polynomial, and $\phi(r) = r$ for biharmonic splines.

12. The method according to claim 11,
wherein $\lambda i$ where $i=1 \ldots n$ are determined so that $s(x)$ satisfies an third equation, $s(xi)=f(xi), i=1, 2, \ldots, n$ and a fourth equation, $$\sum_{j=1}^{n} \lambda_j q(x_i) = 0, \text{ forall} q \in \pi_1^3$$

where $\pi_1^3$ are all three-variable first-order polynomials.

13. The method according to claim 11,
wherein an input smoothing constant $\rho$ is obtained by minimizing a fifth equation, $$\rho \|s\|^2 + \frac{1}{n}\sum_{i=1}^{n}(s(x_i) - f(x_i))^2$$

where $\rho \geq 0$ and $\|s\|^2$ is a measure of an energy in a second derivative of s, and
wherein $\lambda i$ where $i=1 \ldots n$ are determined so that $s(x)$ satisfies a fifth equation, $s(xi)=f(xi)+\rho\lambda i, i=1, 2, \ldots, n$ and a fourth equation, $$\sum_{j=1}^{n} \lambda_j q(x_i) = 0,$$

forall $q \in \pi_1^3$ where $\pi_1^3$ are all three-variable first-order polynomials.

14. The method according to claim 1, wherein the radial basis function is a polyharmonic radial basis function.

15. A non-transitory machine-readable medium storing a computer program for reconstructing a three dimensional model of an object, the computer program operable for:
receiving a plurality of two dimensional images;
segmenting the two dimensional object boundary in each of the two dimensional images, wherein the two dimensional object boundary in each of the two dimensional images is segmented using a deformable contour; and
performing three dimensional fitting of the segmented two dimensional object boundaries using a radial basis function.

16. The machine-readable medium according to claim 15, wherein the plurality of two dimensional images are ultrasound images.

17. The machine-readable medium according to claim 15, wherein the plurality of two dimensional images are transrectal ultrasound (TRUS) images.

18. The machine-readable medium according to claim 17, wherein the TRUS images are formed from signals obtained by a two dimensional TRUS probe.

19. The machine-readable medium according to claim 18, wherein the two dimensional TRUS probe is mounted on a rotational mover.

20. The machine-readable medium according to claim 15, wherein a three dimensional position and an orientation of each of the plurality of two dimensional images are recorded.

21. The machine-readable medium according to claim 15, wherein the plurality of two dimensional images are in transverse axial planes or oblique sagittal and approximately orthogonal planes.

22. The machine-readable medium according to claim 15, wherein the deformable contour is a dynamic deformable contour.

23. The machine-readable medium according to claim 22, wherein the dynamic deformable contour is obtained by dynamically moving each vertex which satisfies a first equation, $f_i^{tot}=w_i^{int}f_i^{int}+w_i^{img}f_i^{img}+w_i^d v_i$, wherein $f_i^{int}$ is an internal or curvature force to maintain contour smoothness, $f_i^{img}$ is an image or external force used to drive contour an edge, $v_i$ is a damping force based on a vertex velocity, and $w_i^{int}$, $w_i^{img}$, and $w_i^d$ are weighting parameters.

24. The machine-readable medium according to claim 15, wherein the step of performing three dimensional fitting using a radial basis function comprises the step of interpolating the segmented two dimensional object boundaries in the plurality of two dimensional images using the radial basis function.

25. The machine-readable medium according to claim 24, wherein the segmented two dimensional object boundaries in the plurality of two dimensional images are interpolated according to a second equation, $$s(x) = p_1(x) + \sum_{i=1}^{n}\lambda_i\phi(\|x - x_i\|), x \in \mathbb{R}^3, \lambda_i \in \mathbb{R}$$

where $s(x)$ is surface approximation of the object, $\rho_1$ is a first order polynomial, and $\phi(r)=r$ for biharmonic splines.

26. The machine-readable medium according to claim 25, wherein $\lambda i$ where $i=1 \ldots n$ are determined so that $s(x)$ satisfies an third equation, $s(xi)=f(xi), i=1, 2, \ldots, n$ and a fourth equation, $$\sum_{j=1}^{n} \lambda_j q(x_i) = 0,$$

forall $q \in \pi_1^3$ where $\pi_1^3$ are all three-variable first-order polynomials.

27. The machine-readable medium according to claim 25, wherein an input smoothing constant $\rho$ is obtained by minimizing a fifth equation, $$\rho \|s\|^2 + \frac{1}{n}\sum_{i=1}^{n}(s(x_i) - f(x_i))^2$$

where $\rho \geq 0$ and $\|s\|^2$ is a measure of an energy in a second derivative of s, and
wherein $\lambda i$, where $i=1 \ldots n$ are determined so that $s(x)$ satisfies a fifth equation, $s(xi)=f(xi)+\rho\lambda i, i=1, 2, \ldots, n$ and a fourth equation, $$\sum_{j=1}^{n} \lambda_j q(x_i) = 0,$$

forall $q \in \pi_1^3$ where $\pi_1^3$ are all three-variable first-order polynomials.

28. The machine-readable medium according to claim 15, wherein the radial basis function is a polyharmonic radial basis function.

29. A method for reconstructing a three dimensional model of an object, comprise the steps of:
- receiving a plurality of two dimensional images;
- segmenting a two dimensional object boundary in each of the two dimensional images; and
- performing three dimensional fitting of the segmented two dimensional object boundaries using a radial basis function, wherein the step of perfoming three dimensional fitting using a radial basis function comprises the step of interloping the segmented two dimensional object boundaries in the plurality of two dimensional images using the radial basis function.

30. The method according to claim 29, wherein the two dimensional object boundary in each of the two dimensional images is segmented using a deformable contour.

31. A non-transitory machine-readable storing a computer program for reconstructing a three dimensional model of an object, the computer program operable for:
- receiving a plurality of two dimensional images;
- segmenting a two dimensional object boundary in each of the two dimensional images; and
- performing three dimensional fitting of the segmented two dimensional object boundaries using a radial basis function, wherein the step of performing three dimensional fitting using a radial basis function comprises the step of interpolating the segmented two dimensional object boundaries in the plurality of two dimensional images using the radial basis function.

32. The machine-readable medium according to claim 31, wherein the two dimensional object boundary in each of the two dimensional images is segmented using a deformable contour.

* * * * *